United States Patent [19]

Schmidt et al.

[11] Patent Number: 4,740,585
[45] Date of Patent: * Apr. 26, 1988

[54] SYNTHETIC VACCINE AGAINST URINARY INFECTIONS

[75] Inventors: M. Alexander Schmidt; Peter O'Hanley; Gary K. Schoolnik, all of Palo Alto, Calif.

[73] Assignee: The Board of Trustees of the Leland Stanford Junior University, Stanford, Calif.

[*] Notice: The portion of the term of this patent subsequent to Apr. 5, 2005 has been disclaimed.

[21] Appl. No.: 635,429

[22] Filed: Jul. 30, 1984

[51] Int. Cl.[4] .................... C07K 7/00; A61K 39/108
[52] U.S. Cl. .................................. 530/300; 530/327; 530/328; 530/806; 530/810; 530/812
[58] Field of Search ............... 424/88, 92; 260/112 R, 260/112.5; 514/2, 14–16; 530/300, 328, 327, 806, 810, 812

[56] References Cited

U.S. PATENT DOCUMENTS 4,554,101 11/1985 Hopp ........................................ 514/2
4,606,919 8/1986 Stogkovic et al. ..................... 424/92

FOREIGN PATENT DOCUMENTS 0048881 4/1982 European Pat. Off.
85/05037 11/1985 PCT Int'l App. ............... 435/172.2

OTHER PUBLICATIONS

O'Hanley et al, Mannose-Sensitive and Gal-Gal Binding E. coli pili . . . Strains, J Exp Med 158, (1983), pp. 1713–1719.
CA. No. 10686312, Strain-Specific and Common Epitopes of Gono-Coocal pili, Jonathan et al, vol.(101), 1984.
Wilson et al, "The Structure of an Antigenis Determinant in a Protein Cell", vol. 37, 1984, pp. 767–778.
Nunberg et al, "Method to Map Antigenic Determinants Recognized . . . Protein pp 70" PNAS 81, 1984, pp. 3675–3679.
Rothbard et al, Current Communication in Molecular Biology, ed Lauer et al, 1985, pp. 161–168.
Snythetis Peptides as Antigens, ed Porter et al, 1986, pp. 184–193 (varies).

Primary Examiner—John Kight
Assistant Examiner—Garnette D. Draper
Attorney, Agent, or Firm—Ciotti & Murashige, Irell & Manella

[57] ABSTRACT

A vaccine effective in protecting mammals against urinary tract infections is prepared from synthetic peptides substantially equivalent to short sequences contained in HU849 pilin conjugated to substantially antigenically neutral carriers or from a CNBrII fragment of HU849 pilin.

9 Claims, 1 Drawing Sheet

---

Primary Protein Structure of HU849 Pilin:

```
1                                                                    20
Ala Pro Thr Ile|Pro Gln Gly Gln Gly Lys Val Thr|Phe Asn Gly Thr Val Val Asp Ala 21                                                                   40
Pro Cys Ser Ile Ser Gln Lys Ser Ala Asp Gln Ser Ile Asp Phe Gly Gln Leu Ser Lys 41                                                                   60
Ser Phe Leu Glu Ala Gly Gly Val Ser Lys Pro Met Asp Leu Asp Ile Glu Leu Val Asn 61                                                                   80
Cys Asp|Ile Thr|Ala Phe Lys Gly Gly Asn Gly Ala Lys Lys Gly|Thr Val Lys Leu Ala 81                                                                   100
Phe Thr Gly Pro Ile Val Asn Gly His Ser Asp Glu Leu Asp Thr Asn Gly Gly Thr Gly 101                                                                  120
Thr Ala Ile Val Val Gln Gly Ala Gly Lys Asn Val Val Phe Asp Gly Ser Glu Gly Asp 121                                                                  140
Ala Asn Thr Leu Lys Asp Gly Glu Asn Val Leu His Tyr Thr Ala Val Val Lys Lys Ser 141                                                                  160
Ser Ala Val Gly Ala Ala Val Thr Glu Gly Ala Phe Ser|Ala Val Ala Asn Phe Asn Leu 161     163
Thr Tyr Gln
```

FIG. 1

Primary Protein Structure of HU849 Pilin:

1
Ala Pro Thr Ile |Pro Gln Gly Gln Gly Lys Val Thr| Phe Asn Gly Thr Val Val Asp Ala 20

21                                                                                40
Pro Cys Ser Ile Ser Gln Lys Ser Ala Asp Gln Ser Ile Asp Phe Gly Gln Leu Ser Lys 41                                                                                60
Ser Phe Leu Glu Ala Gly Gly Val Ser Lys Pro Met Asp Leu Asp Ile Glu Leu Val Asn 61                                                                                80
Cys Asp |Ile Thr |Ala Phe Lys Gly Gly Asn Gly Ala Lys Lys Gly| Thr Val Lys Leu Ala 81                                                                                100
Phe Thr Gly Pro Ile Val Asn Gly His Ser Asp Glu Leu Asp Thr Asn Gly Gly Thr Gly 101                                                                               120
Thr Ala Ile Val Val Gln Gly Ala Gly Lys Asn Val Val Phe Asp Gly Ser Glu Gly Asp 121                                                                               140
Ala Asn Thr Leu Lys Asp Gly Glu Asn Val Leu His Tyr Thr Ala Val Val Lys Lys Ser 141                                                                               160
Ser Ala Val Gly Ala Ala Val Thr Glu Gly Ala Phe Ser| Ala Val Ala Asn Phe Asn Leu 161    163
Thr Tyr Gln

SYNTHETIC VACCINE AGAINST URINARY INFECTIONS

DESCRIPTION

TECHNICAL FIELD

The present invention relates to the field of immunizing humans or animals against urinary tract infection. More specifically, it relates to vaccination of such subjects with short amino acid sequences linked to carriers. These sequences correspond to portions of a protein associated with the pili structures of pathogenic organisms.

BACKGROUND ART

Urinary infections constitute a fairly serious medical problem in the United States and the developed world. Approximately 1–5% of the population of the United States is documented to suffer from recurrent urinary tract infection. Approximately 0.1% of these cases encounter the complication of pyelonephritis. Substantially larger numbers of the population, while not afflicted with recurrent infection, are at potential risk to serious complications, even with one episode of pyelonephritis because of an underlying medical condition. Persons at risk include those who have diabetes mellitus (approximately 10 million in the United States), the elderly, persons with renal insufficiency, users of excessive quantities of analgesics, and persons whose immune systems are suppressed e.g., patients being treated with chemotherapy for neoplasms. All of these individuals are at risk for serious complications, permanent disability, and even death from urinary tract infections.

It would be helpful to provide an effective vaccine which would protect the relevant members of the population from urinary tract infection. Not only would this prevent the suffering and debilitation now occasioned by the onset of actual infection, it also obviates the need for administration of antibiotics which would be required to treat it. Such avoidance lessens the selective pressure on the infectious biomass caused by excessive use of antibiotics, and delays the appearance of resistant strains.

Because the target infections are not usually regarded as imminent life-threatening risks, it is necessary to provide a vaccine which itself offers little or no risk. Materials which have been available heretofore as active ingredients of such vaccines are limited to microorganisms having attenuated pathogenicity and to impure protein preparations which are likely to elicit unwanted immunogenic responses and/or result in undesirable side effects. U.S. Ser. No. 605,287, filed Apr. 30, 1984 discloses a vaccine which is a chemically defined protein comprising particular sequences within HU849 pilin (see below), which is, therefore, noninfectious, and elicits specific antibodies against the organelles of *E. coli* uropathogens responsible for the colonization of the urinary tract, considered the first step in infection. The present invention adds to the repertoire of available immunogens with these advantages, and as an additional benefit, provides a means for eliciting protective action from even very short, easily synthesized sequences.

DISCLOSURE OF THE INVENTION

It has been found that new amino acid sequence fragments homologous with portions of a peptide derived from a specific type of pili associated with most uropathogenic *E. coli*, have desirable properties in acting as the active ingredient in vaccines against urinary tract infections in humans. The "Gal-Gal" pili associated with uropathogenic strains of *E. coli* are highly associated with the targeted infections. Other pili subtypes are not. Accordingly, these additional antigenic domains of the Gal-Gal pilus protein are highly effective and specific in generating antibodies to urinary pathogens, and because of their defined nature and relatively small size, are obtainable in practical quantities and in pure form. In particular, the Gal-Gal pilin which harbors the active peptides of this invention is that of HU849, a transformed recombinant *E. coli* expressing only the gene for Gal-Gal pili, prepared by Hull, et al, *Infect Immun* (1981) 33:933.

Accordingly, in one aspect, the invention relates to a vaccine effective in preventing uropathogenic infections in humans, which vaccine comprises an amino acid sequence substantially equivalent to amino acids 5-12 or to amino acids 65-75 of HU849 pilin, linked to a substantially antigenically neutral carrier. Alternatively the amino acid sequence of the vaccine may be substantially equivalent to amino acids 53-163 of HU849 pilin; no carrier is then needed. The invention also relates to these purified amino acid sequences. In another aspect, the invention relates to protecting humans against urinary infections by administration of the vaccines.

BRIEF DESCRIPTION OF THE DRAWINGS

FIG. 1 shows the amino acid sequence of the Gal-Gal pilus protein of HU849, and the sequences protective against infection according to this invention.

MODES OF CARRYING OUT THE INVENTION

A. Definitions

As used herein, "substantially equivalent to" in characterizing a peptide sequence means that the substantial equivalent is capable of carrying out the same antigenic function and mediating the immunologic function of the referenced sequence. In general, the sequence of amino acids in the substantially equivalent peptide and the referenced peptide will be identical, however, as is well understood, it may be possible to substitute or modify a small number of these residues without appreciable impact on the performance of the resulting polypeptide. Means are now understood in the art for deleting, adding, or modifying individual amino acid residues either directly or by altering their coding sequences, and modifications so performed which result in polypeptide sequences of equivalent performance generate peptides which are "substantially equivalent".

"Peptide", "polypeptide", and "protein" are used interchangeably, and refer to amino acid sequences of a variety of lengths, either in their neutral (uncharged) forms or in forms which are salts, and either free of modifications such as glycosylation, side chain oxidation, or phosphorylation or containing these modifications. It is well understood in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acid side chains, such as glycosyl units, lipids, or inorganic ions such as phosphates, as well as modifications relating to chemical conversions of the chains, such as oxidation of sulfhydryl groups. Thus, "peptide" or its equivalent terms is intended to include the appropriate amino acid sequence referenced, subject to those of the foregoing modifications which do not destroy its immunologic properties.

"Substantially antigenically neutral carrier" refers to a material to which the peptides of the invention may be attached to render them immunogenic, but which does not itself elicit antibodies which will be detrimental to the host, or contain antigenic sites which interfere with the antigenic function of the invention peptides. In the illustration below, as rabbits were used as a source of antibody, bovine serum albumin (BSA) could be used. For human use, however, carriers would be limited to proteins which do not raise antibodies to materials commonly and non-pathogenically encountered by humans. For example, the somatic "Protein I" of the gonococcus itself could be used, as could tetanus toxoid protein. The use of other carriers is not precluded; however, these are the most convenient forms of serologically compatible carriers and are, at the present time, the most conveniently used representatives of this class.

B. General Description of the Invention and Preferred Embodiments

B.1 The Nature of Pilus Protein and Its Relationship to Infection

An essential virulence factor associated with infection is the ability of the infecting bacterium to adhere to its target tissue. This adherence capability appears associated with pili which are proteinaceous surface filamentous structures of the bacterium. These filaments are aggregates of identical subunits (pilin) of moderate sequence length. The *E. coli* which are believed to be associated with uropathogenic infections have at least three types of chromosomally encoded pili: "Common" or "MS"; "Gal-Gal", and "X". They are classified by their binding specificity.

Common (or Type I or mannose binding or MS) pili agglutinate guinea pig erythrocytes and yeast cells and bind the Tamm-Horsfall uromucoid, which is a highly mannosylated glycoprotein secreted by the kidney of all placental mammals. Mannose containing saccharides, such as mannose itself, methyl mannoside, and yeast mannan, competitively inhibit binding. MS pili are found on 85% of all *E. coli* strains regardless of source.

Gal-Gal pili mediate hemagglutination of human erythrocytes in the presence of D-mannose and bind to voided uroepithelial cells. The majority of these strains produce pili that bind to two neutral structurally related glycosphingolipids, globotetraosyl ceramide and trihexosyl ceramide, which are normally present on human erythrocytes and uroepithalial cells. Such pili are found associated with approximately 30% of fecal *E. coli* strains, but are represented in 90-100% of strains isolated from cases of acute, non-obstructive pyelonephritis in children or from the urinary tracts of normal adult women subjects. It has been shown that the disaccharide α-Gal (1-4) β-Gal (Gal-Gal) is the active, minimal receptor recognized by these pili.

The X type pilus protein refers to the remaining proteins which do not fall into either of the two above groups; the nature of their receptors is unknown.

Many *E. coli* strains contain pili of all of the foregoing types. For example, *E. coli* strain J96, an isolate from a human pyelonephritis episode, contains two distinct chromosomal genes encoding pili. These sequences are obtained from restriction digests and isolated. One gene encodes MS pili and the other Gal-Gal pili. Using these fragments, transformed recombinant cells expressing only the gene for MS pili (SH48) and expressing only the gene for Gal-Gal pili (HU849) have been prepared by Hull, et al, Infect Immun (1981) 33:933. Strains containing only MS pili were referred to by Hull as MSHA+, and in particular one such strain was designated HU808; strains containing only Gal-Gal pili were designated MSHA+, in particular one such strain was designated HU807. The numbers HU808 and HU807 correspond to SH48 and HU849, respectively, as used herein. These strains were used as the source of pilus proteins in the examples below. However using analogous techniques, other suitable recombinant strains may be prepared and used as pilin sources; non-recombinant wild type or mutant strains may also be used, if, indeed, they produce the desired pilin.

B.2 Features of the Gal-Gal-Pilus Protein and its Antigenic Determinants

U.S. Ser. No. 605,287 (supra), incorporated herein by reference, sets forth the purification and sequencing of the HU849 pilus protein associated with a typical uropathogen, to give results as shown in FIG. 1. This pilin contains 163 amino acids. As shown by the present invention it contains at least three previously unknown regions of antigenicity. Two of these regions are small, and require conjugation to a carrier peptide in order to become immunogenic—these are sequences substantially equivalent to amino acids 5-12 and to amino acids 65-75 of HU849 pilin. The third region, which corresponds to a CNBr cleavage fragment-amino acids 53-163, is immunogenic alone.

The sequences representing the foregoing fragments can, depending on size, most conveniently be isolated from the digest of purified protein, or can be prepared using recombinant or chemosynthetic techniques. The sequences referred to are intended to correspond approximately to the regions in question, but may contain additional or fewer amino acids so long as immunologic properties are retained. These peptide sequences, conjugated to carrier in the case of the two shorter sequences, are used to prepare vaccines, either as individual active ingredients or in combinations with other immunogens. Antibodies formed in response to the vaccine serve as protection for the subject against subsequent infection by *E. coli* which cause urinary tract infections.

B.3 Preparation of the Polypeptide Active Ingredients

The desired polypeptides which serve as the active ingredients of the vaccines of the invention are most conveniently prepared, depending on their size, by one of three basic approaches.

If the desired sequence is short, e.g., that corresponding to the amino acid sequence constituting positions 5-12 or 65-75 of *E. coli* HU849 pilin—polypeptides having only 8 and 11 amino acids respectively in their sequences—chemical synthesis, using methods now standard in the art, is feasible. A review of such methods is given by, for example, Margolin, A., et al, *Ann Rev Biochem* (1970) 39:841. In most of these procedures, the C-terminal amino acid is bound to a solid support, and reacted with the next amino acid in sequence which has been protected at the amino group to prevent self-condensation. After the initial coupling, the NH$_2$ protecting group is removed, and the coupling process repeated with the amino acid next in order. Polypeptides of considerable chain length have been synthesized in this way. The only requirement is that the amino acid sequence desired to be produced be known.

Since the polypeptides of the invention are produced as part of a larger sequence in the pili or as the pilus protein of bacteria, they are available in quantity from fermenter cultures. They can be prepared by purification of the pilus protein, followed by generation of the desired fragment by various techniques, and purification of the desired fragment. The longer the sequence, the more practical this becomes. Conventional procedures are used in the purification of the pilus protein, in hydrolysis and in fragment purification, and this approach is preferred for preparing the fragment corresponding to amino acids 53-163, which results from a digest of the protein with CNBr designated CNBr-II.

Recombinant DNA methodology provides an alternative way of synthesizing the desired peptides. All three sequences of the invention are amenable to preparation using this technique. The DNA coding sequence for the desired peptide or protein is ligated into an expression vector suitable for transforming a recipient strain, which is thus caused to express the gene and produce the protein. The DNA coding sequences are sufficiently short to be prepared synthetically using means known in the art. Alternatively cDNA or a genomic digest can be used. Since the amino acid sequences are known, appropriate single-stranded DNA probes can be constructed to probe a cDNA library prepared from mRNA of Gal-Gal pilus protein-producing strains. Alternatively, a genomic library can be created by restriction enzyme digests of the chromosome from Gal-Gal pilus protein-producing *E. coli* and probed in a manner similar to that used to probe the cDNA, or the fragments can be directly inserted into expression vectors for transformation into a recipient strain, where successful transformants are screened for production of a protein which binds to Gal-Gal receptors. This was, indeed, the method used by Hull, et al, (supra), to prepare strain HU849.

Whether derived from a genomic or cDNA library, or by oligonucleotide synthesis using chemical methods, the coding sequence is placed under the control of promoter sequences compatible with bacterial hosts in plasmids containing convenient restriction sites for insertion of the desired coding sequence. Typical of such plasmids are, for example, pUC8, and pUC13 available from Messing, J., at the University of Minnesota; (see, e.g., Messing, et al, *Nucleic Acids Res* (1981) 9:309) or pBR322, available from New England Biolabs. Suitable promoters include, for example the β-lactamase (penicillinase) and lactose (lac) promoter systems (Chang, et al, *Nature* (1977) 198:1056 and the tryptophan (trp) promoter system (Goeddel, D., et al, *Nucleic Acids Rec* (1980) 8:4057). The resulting expression vectors are transformed into suitable bacterial hosts using the calcium chloride method described by Cohen, S. N., et al, *Proc Natl Acad Sci* (U.S.A.) (1972) 69:2110. Successful transformants may produce the desired polypeptide fragments at higher levels than those found in recombinant or native strains normally producing Gal-Gal pili. Alternatively, these peptides can be produced in nonbacterial recombinant hosts using appropriate control sequences, vectors and transformation techniques.

B.4 Linkers

Because the peptide sequences represented by amino acids 5-12 and 65-75 are considered too small to be immunogenic, they have been linked to carrier substances in order to confer this property upon them. Any method of creating such linkages known in the art may be used.

Linkages can be formed in a variety of ways. For example, there are a large number of heterobifunctional agents which generate a disulfide link at one functional group end and a peptide link at the other, and these have been used extensively. The most popular of these is N-succidimidyl-3-(2-pyridyldithio) proprionate (SPDP). This reagent creates a disulfide linkage between itself and a cysteine residue in one protein and an amide linkage through the amino on a lysine, or other free amino group in the other. A variety of such disulfide/amide forming agents are known. See for example *Immun. Rev.* (1982) 62:185. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. The particularly preferred coupling agent for the method of this invention is succinimmidyl 4-(N-maleimido-methyl) cyclohexane-1-carobxylate (SMCC) obtained from Pierce Company, Rockford, Illinois. The foregoing list is not meant to be exhaustive, and modifications of the named compounds can clearly be used. If the peptide contains no convenient cysteine, an additional cysteine residue at either terminus is added when the peptide is prepared. As only shorter peptides require conjugation to carrier, these residues can be included conveniently during chemical synthesis.

B.5 Vaccine Preparation

Preparation of vaccines which contain peptide sequences as active ingredients are well understood in the art. Typically, such vaccines are prepared as injectables, either as liquid solutions or suspensions; solid forms suitable for solution or suspension in liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of manitol, lactose, starch, magnesium sterate, sodium saccharrine, cellulose, magnesium carbonate and the like. These compositions take the form of solutions, suspensions, tablets, pills, capsules, sustained release formulations or powders and contain 10%–95% of active ingredient, preferably 25–70%.

As is understood in the art, the proteins of the present invention are present as neutral or salt forms depending on the pH of the surrounding medium, or of the medium from which they have been precipitated or crystallized. Accordingly, the amino acid sequences of the invention include their pharmaceutically acceptable salts, including the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges for subcutaneous or muscular injection are of the order of 50–500 µg active ingredient per individual. For oral, rectal suppository, urethral or vaginal preparation, large amounts of about 100 µg-1mg would be used. Suitable regimes for initial administration and booster shots are also variable, but are typified by an initial administration followed in one-two week intervals by a subsequent injection or other administration.

EXAMPLES

The following serve to illustrate but not to limit the invention.

C.1 Isolation of Amino Acid Sequence 53-163.

Pili from HU849 were purified from organisms grown on TSA for 18 hours at 37° C., basically according to the method of Brinton, C. *Trans N Y Acad Sci* (1965) 27:1003. Briefly, the cells were harvested into ice-cold 0.005 M Tris buffer, pH 8.3 (T-buffer). Pili were sheared from the bacterial surface in a Sorval Omnimixer (4000 rpm for 30 minutes at 4° C.) and depiliated organisms and debris were removed by centrifugation. The pili were precipitated in 0.5 M Tris buffer and 0.15 M NaCl, pH 7.0, by the addition of $MgCl_2$ to 0.1 M (TSM buffer). The aggregated pilus fragments were then collected by centrifugation, the pellet was dissolved in T-buffer and insoluble impurities removed by centrifugation.

The pili were re-precipitated in TSM buffer and separated from soluble impurities by centrifugation. After 6 cycles of precipitation and solubilization in TSM and T-buffer respectively, the pilin preparations were extensively dialyzed against double-distilled deionized water.

The purity of the resulting proteins was confirmed by electron microscopy, SDS-PAGE, amino terminal sequence analysis, and by assessment of the level of lipopolysaccharide (LPS) contamination.

For electron microscopy samples were negatively stained with 2% (w/v) aqueous uranyl acetate on copper grids coated with Formvar and carbon.

SDS-PAGE was performed according to the method of Laemmli *Nature* (1970) 227:680. Gels were stained with Coomassie brilliant blue R250 (Sigma Chemical Co., St. Louis, MO) or silver (Morrissey, J., *Anal Biochem* (1982) 117:307) for protein detection; and also oxidized with periodic acid and then silver stained (Tsai, G.M., et al, *Anal Biochem* (1982) 119:115) for the detection of contaiminating LPS.

LPS was also estimated by determining the 2-keto-3-deoxy-D-manno-octonate content of 500 to 1000 µg samples using the method of Waravdekar, V., et al, *J Biol Chem* (1959) 234:1945 by relating their optical density at 548 nm to standard curves derived from LPS prepared from *E. coli* strains HB101 and J96 by the phenol-extraction method of Westphal, O., et al, *Meth Carbohyd Chem* (1965) 5:80.

N-terminal sequencing was performed by automated Edman degradation with a Beckman 890C liquid-phase sequencer (Beckman Instruments, Palo Alto, CA) using a 0.1 M Quadrol program. Each amino acid phenylthiohydantoin (PTH) derivative was identified and quantitated by reverse-phase high pressure liquid chromatography and confirmed by gas-liquid chromatography and/or thin-layer chromatography.

The purified pilus protein preparation was found to be free of both RNA and DNA and to be 97–99% homogeneous according to SDS-PAGE. These preparations were confirmed by electron microscopy to be composed of homologous filaments with minimal non-filamentous structures. The LPS content was less than 0.1% as measured by the 2-keto-3-deoxy-D-manno-octonate (KDO) assay and less than 0.01% as assessed by lack of silver stain corresponding to LPS on gels.

The purified pilus protein was treated with CNBr using standard techniques, and the fragments purified by application to a C-18 reverse phase HPLC column and eluted in 0.1% trifluoroacetic acid buffer using a 0–80% acetonitrile linear gradient. Protein containing fractions were further purified using high voltage paper electrophoresis in pyridine/acetate buffer, pH 6.4.

The CNBr fragment corresponding to amino acids 53-163 obtained using the foregoing methods was confirmed to behave as an antigenic determinant, by Western Blot performed as described by Towbin, H., et al, *Proc Natl Acad Sci* (U.S.A.) (1979) 76:4350 or Swanson, J., et al, *Infect Immun* (1982) 38:668, and using rabbit antisera against HU849 pilin.

C.2 Preparation of Sequences 5-12 and 65-75.

The peptide Pro-Gln-Gly-Gln-Gly-Lys-Val-Thr was synthesized on a commercial Beckman Model 990B Peptide Synthesizer using commerically available amino acid polystyrene resins and t-Boc protected amino acids (Peninsula Laboratories, Belmont, Calif.), with the following side chain protecting groups: O-benzyl esters for Asp, Glu, Thr, and Ser; tosyl for Arg and His; p-methoxybenzyl for Cys, o-chlorobenzyloxycarbonyl for Lys, and 2, 6-dichlorobenzyl for Tyr. Coupling was performed using a 2.5 molar excess of t-Boc amino acid and dicyclohexylcarbodiimide (DCC) over resin bound amino acid. In the case of Asn and Gln, a 2.5 molar excess of the amino acid, DCC, and N-hydroxytriazole was used. All couplings were more than 99% complete, as determined by the reaction of the resin with ninhydrin. The peptides were simultaneously deprotected and removed from the resin by treatment with anhydrous HF in the presence of anisole, dimethylsulfide, and indole. The peptides were separated from the various organic side products by extraction with ether, isolated from the resin by extraction with 5% acetic acid and then lyophilized. The purity of the crude product was determined by HPLC on a C-18 reverse phase column (Merck, Darmstadt, Germany) and by amino acid analysis. The peptide was determined to be more than 90% pure.

In a similar manner the following peptides were prepared: Pro-Gln-Gly-Gln-Gly-Lys-Val-Thr-Cys, Ala-Phe-Lys-Gly-Gly-Asn-Gly-Ala-Lys-Lys-Gly, and Ala-Phe-Lys-Gly-Gly-Asn-Gly-Ala-Lys-Lys-Gly-Cys.

C.3 Linkage to Carrier Protein

The peptides from C.2 which contained a C-terminal Cys residue were linked to bovine serum albumin using succinimidyl 4-(N-maleimidomethyl) cyclohexane-1-carboxylate (SMCC) (Pierce, Rockford, Ill.) as described by Yoshitake, S. et al, *Eur J. Biochem.* (1979) 101: 395. Briefly, 10 mg BSA were dissolved in 2 ml phosphate buffered saline (PBS), pH 7.4 and combined with 5 mg of SMCC in 0.5 ml of dimethylformamide. After one hour at room temperature, the conjugate was separated from unreacted SMCC by gel filtration on G-25 in 0.1 M phosphate, pH 6.0.

The peptide Pro-Gln-Gly-Gln-Gly-Lys-Val-Thr-Cys was dissolved in 0.1 M borate, pH 9.1 and reduced with NaBH$_4$ (0.1 ml of 0.1 M stock). After five minutes, the pH of the borate solution was lowered to 1 with 1 M HCl to remove excess NaBH4 and then raised to pH 6 with 1 M NaOH, and combined with the linker-BSA conjugate. After incubating at room temperature for an additional hour, the peptide-linker-BSA conjugate was desalted on a G-25 column in 0.1 M NH$_4$HCO$_3$. The degree of conjugation was quantitated by comparing the amino acid composition of the BSA before and after reaction with the peptide. The conjugate contained approximately 15-25 peptides per molecule of BSA.

In a similar manner, the other C-terminal Cys containing peptide of C.2 was conjugated with BSA.

C.4 Balb/C Model for Pyelonephritis and Immunization Assay

Urinary tract infections in general can be exemplified by pyelonephritis. In the course of this disease, the bacteria enter the urinary tract, adhere to and colonize the mucosa, and ultimately infect the host.

A model for this disease in Balb C mice which can be used to study the parameters of the disease in human subjects has been established by O'Hanley, U.S. Ser. No. 605,287 (supra). Challenge is made by administering $10^8$ colony forming units (CFU) of *E. coli* J96 by intra-urethral catheterization. Progress (or lack thereof) of the infection is monitored by assessing the urine and renal growth as follows:

Two days after challenge the mice were killed by prolonged ether anesthesia, and both urine and kidney tissues were assayed for the presence of bacterial growth. To assay urine, the bladder area was massaged to express urine, and a sterile 10 μl loop used to inoculate 0.5 cm$^2$ trypticase soy agar (TSA) or TSA supplemented with antibiotics. The plates were incubated for 18-24 hours at 37° C. and read by grading the visible growth. The identity of the growth observed as *E. coli* J96 with the administered strain was verified if the organisms grown on TSA plates were predominantly gram-negative and agglutinated by rabbit anti-J96 O sera (1:1000 dilution in PBS) in a slide agglutination assay.

Kidneys were excised by sterile techniques and sagitally sectioned through the mid-pelvis, and a cut surface was streaked onto a TSA or antibiotic supplemented TSA. The remainder of the assay was as described for urine samples in the previous paragraph.

C.5 Protection by Peptides of the Invention

The test vaccines employed the peptides corresponding to amino acids 5-12 or 65-75 conjugated to substantially antigenically neutral carrier as prepared in C.3, or the CNBrII fragment from purified HU849 pilin as described in C.1. Control vaccines were prepared from HU849 pili and from alternate synthetic peptides linked to carrier. A buffer control was also used.

The vaccines were prepared using 50 μg of protein "active ingredient" in 1 ml PBS, pH 7.4, emulsified with 1 ml of complete Freund's adjuvant. The resulting 2 ml of vaccine was administered in multiple subcutaneous and intramuscular injections.

The animals were challenged after two weeks by administration of $10^8$ CFU *E. coli* J96 in 100 μl by intra-urethral catheterization as described in C.4. Two days later, the mice were exsanguinated, and sera obtained for antibody titer and kidneys were excised and sagitally sectioned through the mid-portion to assess specifically for J96 colonization as described above.

The results shown in the table below, indicate the ratio of the number of animals showing positive J96 colonization or invasion to the number of mice.

| Vaccination Trial with a Variety of Immunogens in the Prevention of *E. coli* Pyelonephritis | | | | |
|---|---|---|---|---|
| | J96 Colonization | | | |
| | +Urine | | +R Kidney | |
| Immunogen | #mice | Density | #mice | Density |
| Buffer Control | 8/8 | 4.8 | 8/8 | 3.3 |
| HU849 pili | 3/19 | 0.3 | 1/19 | 0.1 |
| CNBrII (63-153) | 0/7 | 0.0 | 0/7 | 0.0 |
| Carrier: peptide (residues 5-12) | 0/11 | 0.0 | 0/11 | 0.0 |
| Carrier: peptide (residues 65-75) | 3/8 | 0.4 | 0/8 | 0.0 |
| Carrier: peptide (residues 131-143) | 15/15 | 4.8 | 15/15 | 3.8 |
| Carrier: peptide (residues 103-116) | 8/8 | 5.0 | 8/8 | 4.5 |

Attempts to protect mice from challenges against J96 infection vaccination using control sequences corresponding to amino acids 131-143 or 103-116 failed uniformly by every criterion tested. The vaccines prepared from the 5-12 and 65-75 peptides linked to carrier and from the CNBr-II fragment were effective.

We claim:

1. A peptide of the sequence selected from the group consisting of a Pro Gln Gly Gln Gly Lys Val Thr and Pro Gln Gly Gln Gly Lys Val Thr Cys, in substantially pure form.

2. A peptide of the sequence selected from the group consisting of Ala Phe Lys Gly Gly Asn Gly Ala Lys Lys Gly and Ala Phe Lys Gly Gly Asn Gly Ala Lys Lys Gly Cys, in substantially pure form.

3. The peptide of claim 1 conjugated to a substantially antigenically neutral carrier.

4. The peptide of claim 2 conjugated to a substantially antigenically neutral carrier.

5. A vaccine protective against urinary tract infections in mammals which comprises an effectively protective amount of a peptide consisting essentially of an amino acid sequence selected from the group consisting of:
Pro Gln Gly Gln Gly Lys Val Thr; and
Ala Phe Lys Gly Gly Asn Gly Ala Lys Lys Gly;
conjugated to a substantially antigenically neutral carrier.

6. The vaccine of claim 5 wherein the peptide further contains a Cys residue at one of its termini.

7. A vaccine protective against urinary tract infections in mammals which comprises an effectively protective amount of a peptide consisting essentially of the amino acid sequence Asp Leu Asp Ile Glu Leu Val Asn Cys Asp Ile Thr Ala Phe Lys Gly Gly Asn Gly Ala Lys Lys Gly Thr Val Lys Leu Ala Phe Thr Gly Pro Ile Val Asn Gly His Ser Asp Glu Leu Asp Thr Asn Gly Gly Thr Gly Thr Ala Ile Val Val Gln Gly Ala Gly Lys Asn Val Val Phe Asp Gly Ser Glu Gly Asp Ala Asn Thr Leu Lys Asp Gly Glu Asn Val Leu His Tyr Thr Ala Val Val Lys Lys Ser Ser Ala Val Gly Ala Ala Val Thr Glu Gly Ala Phe Ser Ala Val Ala Asn Phe Asn Leu Thr Tyr Gln.

8. A method of protecting a subject mammal against urinary tract infection which comprises administering to a mammal in need of such protection a protectively effective amount of the vaccine of claim 5.

9. A method of protecting a subject mammal against urinary tract infection which comprises administering to a mammal in need of such protection a protectively effective amount of the vaccine of claim 7.

* * * * *